US012778956B2

(12) United States Patent
He et al.

(10) Patent No.: US 12,778,956 B2
(45) **Date of Patent: *Nov. 3, 2026**

(54) PROCESS FOR IMPROVING FLUIDITY OF PALBOCICLIB ISETHIONATE AND COMPOSITION

(71) Applicant: NANJING GRITPHARMA CO., LTD., Nanjing (CN)

(72) Inventors: Hongyan He, Nanjing (CN); Qianqian Zhang, Nanjing (CN); Jiannan Yang, Nanjing (CN); Yazhou He, Nanjing (CN); Yizhang Zuo, Nanjing (CN); Lu Zhao, Nanjing (CN); Weiye Wei, Nanjing (CN); Liru Huo, Nanjing (CN); Zhan Li, Nanjing (CN)

(73) Assignee: NANJING GRITPHARMA CO., LTD., Nanjing (CN)

( * ) Notice: Subject to any disclaimer, the term of this patent is extended or adjusted under 35 U.S.C. 154(b) by 736 days.

This patent is subject to a terminal disclaimer.

(21) Appl. No.: 18/246,463

(22) PCT Filed: Nov. 9, 2020

(86) PCT No.: PCT/CN2020/127405

§ 371 (c)(1),
(2) Date: Mar. 23, 2023

(87) PCT Pub. No.: WO2022/062096

PCT Pub. Date: Mar. 31, 2022

(65) Prior Publication Data

US 2023/0355631 A1 Nov. 9, 2023

(30) Foreign Application Priority Data

Sep. 24, 2020 (CN) ......................... 202011017490.8

(51) Int. Cl.

| | |
|---|---|
| ***A61K 31/519*** | (2006.01) |
| ***A61K 9/16*** | (2006.01) |
| ***A61K 9/48*** | (2006.01) |

(52) U.S. Cl.

CPC .......... *A61K 31/519* (2013.01); *A61K 9/1611* (2013.01); *A61K 9/1635* (2013.01); *A61K 9/1652* (2013.01); *A61K 9/1694* (2013.01); *A61K 9/4825* (2013.01); *A61K 9/485* (2013.01)

(58) Field of Classification Search

CPC .. A61K 31/519; A61K 9/1611; A61K 9/1635; A61K 9/1652; A61K 9/1694; A61K 9/4825; A61K 9/485; A61K 9/1623; A61K 9/1682; A61P 35/00

See application file for complete search history.

(56) References Cited

U.S. PATENT DOCUMENTS

2018/0280392 A1* 10/2018 Zeng .................... A61K 9/4858

FOREIGN PATENT DOCUMENTS

| | | | | |
|---|---|---|---|---|
| CN | 104189915 A | | 12/2014 | |
| CN | 105213322 A | | 1/2016 | |
| CN | 106667952 A | * | 5/2017 | ........... A61K 9/4858 |
| CN | 107666914 A | | 2/2018 | |
| CN | 105748435 A | | 3/2019 | |
| WO | 2019020715 A1 | | 1/2019 | |

OTHER PUBLICATIONS

International Search Report dated Jun. 23, 2021 for International Application No. PCT /CN2020/127405.

* cited by examiner

*Primary Examiner* — Jessica Worsham

(57) ABSTRACT

The present invention discloses a process for improving the fluidity of palbociclib isethionate and a composition, and belongs to the field of pharmaceutical preparations. The process includes a step of conducting granulation on palbociclib isethionate and pharmaceutically acceptable auxiliary materials to obtain granules with a tap density of 0.55-0.72 g/mL and an angle of repose of less than or equal to 44°. According to the process of the present invention, the palbociclib isethionate composition has good granular fluidity during filling of capsules, and prepared palbociclib isethionate capsules have uniform content, good stability and controllable quality. A preparation method is convenient to operate and easy to understand and adjust, and has good controllability in expanded production.

9 Claims, 2 Drawing Sheets

PROCESS FOR IMPROVING FLUIDITY OF PALBOCICLIB ISETHIONATE AND COMPOSITION

TECHNICAL FIELD

The present invention relates to a pharmaceutical preparation and a preparation method thereof, specifically relates to a process for improving the fluidity of palbociclib isethionate and a composition, and belongs to the technical field of medicine.

BACKGROUND

Breast cancer is one of major malignant tumors endangering the health of women in the global world. According to a report of International Agency for Research on Cancer of World Health Organization, about 1.677 million new cases of female breast cancer were found in the global world in 2012, accounting for 25.2% of female malignant tumors; the age-standardized incidence of the female breast cancer in the global world was 43.3/100,000, ranking the 1st in the incidence of the female malignant tumors; and the age-standardized mortality of the female breast cancer in the global world was 12.9/100,000, ranking the 1st in order in causes of death of the female malignant tumors. The breast cancer has become a major public health issue in current society. In the past 20 years, China has made no significant progress in medicines for treatment of advanced breast cancer, and is lack of innovative breakthrough therapies. Patients with the advanced breast cancer have an overall median survival time of only 2-3 years and a 5-year survival rate of only about 20%. Thus, innovative therapy programs are urgently in need. The emergence of a CDK4/6 inhibitor is a major process in the treatment of HR+ advanced breast cancer. According to clinical studies, it has been proven that compared with single use of endocrinotherapy, combined use of the CDK4/6 inhibitor can achieve obvious PFS benefits, and meanwhile good tolerance is achieved.

Palbociclib is the first inhibitor of cyclin-dependent kinases (CDK) 4 and 6 in the global world that is developed by Pfizer and approved by the FDA of the United States for marketing. Cyclin D1 and CDK4/6 are located in the downstream of a cell proliferation signaling pathway. The palbociclib blocks the conversion of cells from a G1 phase into an S phase, so as to reduce the proliferation of estrogen receptor (ER)-positive breast cancer cell lines. Through combined use of the palbociclib and an estrogen receptor antagonist in breast cancer cells, phosphorylation of retinoblastoma (Rb) protein can be reduced, so that the expression of E2F and the signal transduction are reduced. Compared with single use of each medicine, the growth inhibition effect is improved. When the palbociclib and the estrogen receptor antagonist are combined for use in ER-positive breast cancer cells, cell senescence is increased in comparison with the single use of each medicine, and the effect is maintained for at most 6 days after the palbociclib is not used. However, the cell senescence may be caused to a larger extent when anti-estrogen treatment is continued. According to in vivo studies of a human ER-positive breast cancer xenograft model, it is shown that compared with the single use of each medicine, combined use of the palbociclib and letrozole can improve an inhibitory effect on the phosphorylation of Rb, the signal transduction in the downstream and the growth of tumors. When the palbociclib is provided for human bone marrow mononuclear cells with or without anti-estrogen treatment, cell senescence does not occur, and proliferation is recovered after the palbociclib is not used.

The palbociclib was granted a “breakthrough therapy” certificate by the FDA of the United States in April 2013. In February 2015, IBRANCE® (palbociclib) was approved by the FDA at an accelerated pace based on breakthrough therapy certification and priority review programs, which has become a standard therapy for first-line treatment of advanced or metastatic breast cancer in the United States. By means of the innovative medicine, an innovative treatment option is provided for patients with HR+/HER2− advanced breast cancer, the progression-free survival time of the patients can be obviously prolonged, the life quality of the patients is improved, and meanwhile patient families and the society are also benefited. The palbociclib is used in an isethionate form by Pfizer in non-clinical studies and early clinical studies. However, in a development process of medicine products, it has been found that a bulk drug of isethionate is a loose power, which is easy to adhere and agglomerate and has poor fluidity, it was difficult for the content uniformity of preparation products prepared to meet standard requirements, and in particular, the uniformity is more difficult to control in a production scale environment. When capsules are filled in commercial batches in a large scale, the problem of difficulty in automatic filling of capsules at high speed will be caused due to poor fluidity. Therefore, commercial development of the isethionate is abandoned by Pfizer, and the isethionate is changed into a specific free alkali crystal form.

SUMMARY

1. Problems to be Solved

Aiming at the problems of poor fluidity of a raw material of palbociclib isethionate and difficulty in application to large-scale manufacturing in the prior art, the present invention provides a process for improving the fluidity of palbociclib isethionate and a composition. In combination with the quality-by-design concept, a palbociclib isethionate composition with good fluidity is obtained by a premixing step in a preparation process of the composition and control of the tap density and angle of repose of granules in dry granulation. Meanwhile, it can be ensured that the composition has in vitro dissolution behaviors similar to that of free alkali. According to the process, convenience is provided for commercial development of the palbociclib isethionate in a large scale.

2. Technical Solutions

In order to solve the above problems, the present invention adopts the following technical solutions.

The present invention provides a process for improving the fluidity of palbociclib isethionate and a composition. The palbociclib isethionate is mixed with auxiliary materials, the auxiliary materials with good fluidity are used for improving the fluidity of the palbociclib isethionate in advance, and then granulation is conducted to tighten a loose powder, so that the fluidity of the palbociclib isethionate is further improved. According to the operation process, the fluidity of the palbociclib isethionate is improved, the process can be applied to filling of capsules or preparation of tablets in a large scale, and the problems about parameter control in a production process and uniformity of key quality attributes in a mass production process are successfully solved. A preparation method is convenient to operate and easy to understand and adjust, and a product has stable and controllable quality and is convenient to produce in a large scale.

A first object of the present invention is to provide a process for improving the fluidity of palbociclib isethionate. The process includes a step of conducting granulation on palbociclib isethionate and pharmaceutically acceptable auxiliary materials to obtain granules with a tap density of 0.55-0.72 g/mL and an angle of repose of less than or equal to 44°.

Further, the tap density is preferably 0.62-0.69 g/mL.

Further, the auxiliary materials include a diluent, a disintegrant and a lubricant.

Further, the auxiliary materials further include a glidant. The fluidity problem is further solved by combining the glidant and the lubricant or adding the lubricant separately, so as to achieve a better capsule filling effect.

Further, the palbociclib isethionate is premixed first with the diluent;

and a premix obtained after premixing is mixed with other auxiliary materials, dry granulation is conducted to obtain granules before filling of capsules, where the granules before filling of capsules have a tap density of 0.55-0.72 g/mL and an angle of repose of less than or equal to 44°, and then capsules are filled, and where the palbociclib isethionate is premixed first with the diluent, so that the palbociclib isethionate is adsorbed by the diluent and uniformly dispersed in the diluent;

or a premix obtained after premixing is mixed with other auxiliary materials except for the glidant and the lubricant, dry granulation is conducted to obtain dry granulated granules, the glidant and the lubricant are added for mixing to obtain granules before filling of capsules, where the granules before filling of capsules have a tap density of 0.55-0.72 g/mL and an angle of repose of less than or equal to 44°, and then capsules are filled;

or a premix obtained after premixing is mixed with other auxiliary materials except for the lubricant, dry granulation is conducted to obtain dry granulated granules, the lubricant is added for mixing to obtain granules before filling of capsules, where the granules before filling of capsules have a tap density of 0.55-0.72 g/mL and an angle of repose of less than or equal to 44°, and then capsules are filled.

Further, a mass ratio of the palbociclib isethionate to the diluent during premixing is 1: (0.8-2.0).

Further, before the dry granulation, the premix is mixed with other auxiliary materials in a three-dimensional motion mixer for 10-30 min. The other auxiliary materials herein include auxiliary materials except for the diluent, or other auxiliary materials except for the diluent, the glidant and the lubricant, or other auxiliary materials except for the diluent and the lubricant.

Further, the dry granulation is conducted by using a GL5-50 dry granulation machine with a 2.0 mm primary granulation sieve and a 1.0 mm secondary granulation sieve at a press roll pressure of 25-65 kg/cm$^3$.

Further, before the palbociclib isethionate is premixed first with the diluent, the process further includes: a step of sifting the palbociclib isethionate, the disintegrant, the diluent, the lubricant and the glidant for later use.

Further, in the premixing step, when a composition contains one diluent, the palbociclib isethionate is premixed first with the diluent completely, and then sifting is conducted to obtain a premix; and when a composition contains two or more diluents, the palbociclib isethionate is premixed first with all the diluents, or the palbociclib isethionate is premixed first with one of the diluents, and then sifting is conducted to obtain a premix.

Further, in the premixing step, when a composition contains two or more diluents, the palbociclib isethionate is premixed first with one diluent with the highest content among the diluents, and then sifting is conducted to obtain a premix.

It should be noted that the granules obtained in the granulation step of the present invention may be the granules obtained after the dry granulation (dry granulated granules), or the granules obtained after the dry granulation and mixing, namely the granules before filling of capsules.

Further, the diluent is selected from one or more of lactose, microcrystalline cellulose, pregelatinized starch, mannitol or calcium hydrogen phosphate.

Further, the diluent is preferably microcrystalline cellulose, and more preferably highly porous granular microcrystalline cellulose.

Further, the disintegrant is selected from one or more of crospovidone, sodium carboxymethyl starch, crosslinked sodium carboxymethyl cellulose, calcium carboxymethyl cellulose or low-substituted hydroxypropyl cellulose.

Further, the lubricant is selected from one or more of magnesium stearate, sodium stearyl fumarate, calcium stearate and stearic acid.

Further, the glidant is selected from one or more of silicon dioxide, talc powder or polyethylene glycol.

Further, a composition includes 40-70 parts by mass of the diluent, 1-15 parts by mass of the disintegrant, 0.1-10 parts by mass of the lubricant, 0-10 parts by mass of the glidant, and 25-50 parts by mass of the palbociclib isethionate.

Further, 50-60 parts by mass of the diluent, 3-10 parts by mass of the disintegrant, 0.5-4 parts by mass of the lubricant, 0.5-5 parts by mass of the glidant, and 30-45 parts by mass of the palbociclib isethionate are used.

The present invention further provides a composition prepared by the process above.

3. Beneficial Effects

Compared with the prior art, the present invention has the following beneficial effects.

(1) The present invention aims at the problems that the palbociclib isethionate has poor fluidity and is a loose powder. When capsules are filled, especially when capsules are filled in commercial batches in a large scale, the problem of difficulty in automatic filling at high speed will be caused due to poor fluidity. After a lot of studies, it has been found that the phenomenon is difficult to reduce by simply adding auxiliary materials. It has been found through studies that the problem can be better solved by adopting the step of conducting granulation on palbociclib isethionate and pharmaceutically acceptable auxiliary materials and controlling granules obtained after the granulation to have a tap density of 0.55-0.72 g/mL and an angle of repose of less than or equal to 44°. The tap density of the granules obtained after the granulation is further preferably in the range of 0.62-0.69 g/mL, and a palbociclib isethionate composition sample which has good fluidity and is easy to fill and process can be obtained.

(2) According to the process of the present invention, due to small particle size, easy agglomeration and difficult sifting of the palbociclib isethionate in a preparation process, the content uniformity of the palbociclib isethionate in composition products is affected. The process of combining premixing of the palbociclib isethionate with the diluent, sifting and dry granulation is further adopted, and the premixing step is adopted to ensure that products with uniform content are obtained.

(3) The diluent in the present invention is preferably highly porous granular microcrystalline cellulose, which is a granular substance with appearance and properties as shown in FIG. 3 (SEM). First, the highly porous granular microcrystalline cellulose has an excellent bonding force. According to the technical solutions of the present invention, the dry granulation can be conducted directly without adding other binders, and press forming can be ensured at low press roller pressure during the dry granulation. Moreover, the highly porous microcrystalline cellulose is added to achieve an anti-bonding effect, so that the dose of the lubricant can be reduced. Second, medicines with small particle size can be firmly adsorbed by pores in granules to achieve a spheroidization effect, and the palbociclib isethionate which is easy to aggregate is dispersed so as to be easily sifted and dispersed uniformly. Third, due to a porous structure of the highly porous granular microcrystalline cellulose, after the microcrystalline cellulose gets contact with a liquid, water can rapidly enter the microcrystalline cellulose to achieve a capillary effect, so as to promote rapid disintegration and action of the medicines in the pores.

(4) A material is compressed by rollers of a dry granulation apparatus at certain pressure. After the granulation, the looseness of the powder is changed, and the fluidity is improved, so that subsequent filling of capsules can be conducted easily. Even raw materials with small particle size can be better filled after the dry granulation in the present invention, and meanwhile the problem of large amounts of dust generated by a direct powder filling process is avoided.

(5) Through the mixing of the palbociclib isethionate with the auxiliary materials and the dry granulation, the fluidity is greatly improved. The palbociclib isethionate can be applied to automatic filling by a capsule filling machine in a large scale. The problems about parameter control in a production process and uniformity of key quality attributes in a mass production process are successfully solved. The process has no special requirements for production conditions. A preparation method is convenient to operate and easy to understand and adjust, and has good controllability in expanded production. Industrialization can be realized.

(6) Palbociclib isethionate capsules prepared by the process of the present invention have in vitro dissolution behaviors basically consistent with that of free alkali palbociclib capsules in a medium with a pH of 1.2. According to investigation in a stability test, data show that finished products of preparations have stable and reliable quality.

DETAILED DESCRIPTION

Figure 1:
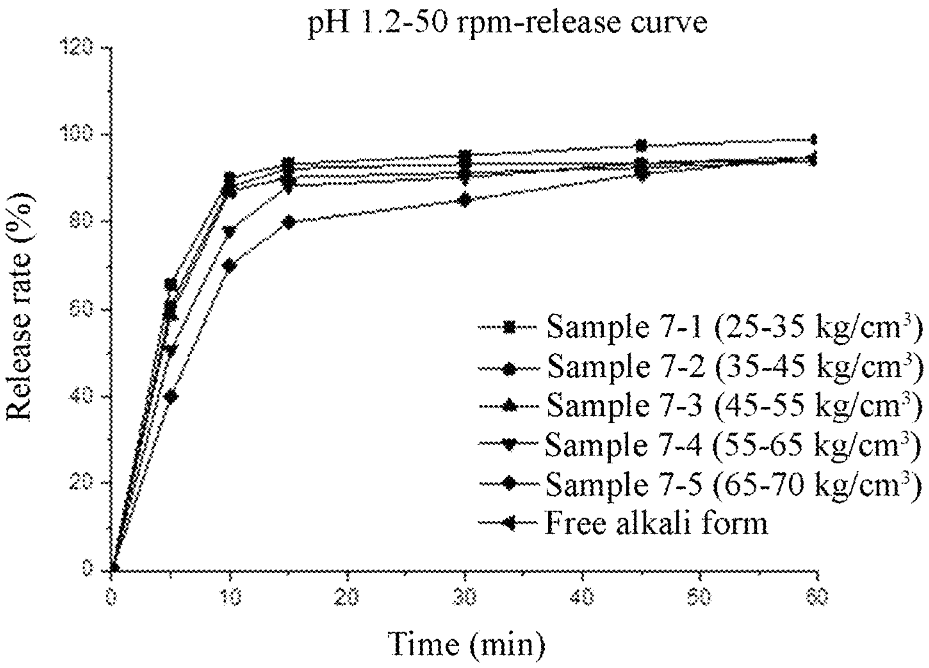
FIG. 1 shows release curves of 5 batches of samples in Example 7 in a medium with a pH of 1.2.

Unless otherwise defined, meanings of all technical and scientific terms used herein are the same as those usually understood by a person skilled in the art to which the present invention belongs. The term "and/or" used herein includes any or all combinations of one or more of related listed items.

When specific conditions are not specified in embodiments, processes shall be carried out in accordance with conventional conditions or conditions suggested by manufactures. All reagents or instruments used without specific manufacturers are commercially available conventional products.

As used herein, the term "about" is used for providing flexibility and imprecision associated with a given term, measure, or value. The degree of flexibility of specific variables can be easily determined by a person skilled in the art.

Parts, concentrations, quantities, and other numerical data can be presented in the form of a range herein. It should be understood that the form of a range is used only for convenience and brevity, and should be interpreted flexibly to include not only values that are explicitly stated as limits of the range, but also all individual values or subranges that are covered within the range, as if each value and subrange are explicitly stated. For example, the numerical range from about 1 to about 4.5 should be interpreted to include not only explicitly stated limits from 1 to about 4.5, but also individual numbers (such as 2, 3, and 4) and subranges (such as 1 to 3 and 2 to 4). The same principle is applicable to ranges that state only one value, such as "less than about 4.5," which should be interpreted to include all of the above values and ranges. In addition, the interpretation should apply regardless of the scope or breadth of features described.

Any steps described in any method or process claims may be carried out in any order, and are not limited to the order set forth in the claims. Limitations of a method and a function or a step and a function are adopted only when all of the following conditions are satisfied in a specific claim limitation: a) a "method for . . . " or a "step for . . . " is explicitly stated; and b) corresponding functions are explicitly stated. Structures, materials, or actions that support a method and a function are explicitly stated in the description herein. Therefore, the scope of the present invention shall be determined only by the attached claims and legal equivalents thereof and not by the description and embodiments provided herein.

The present invention is further described below in conjunction with specific embodiments.

Example 1

A prescription includes the following components:

| | | |
|---|---|---|
| Palbociclib isethionate | 160.23 | g |
| Lactose | 82.7 | g |
| Microcrystalline cellulose (JRS12) | 165.4 | g |
| Crospovidone | 27 | g |
| Colloidal silicon dioxide | 5.7 | g |
| Magnesium stearate | 9 | g |
| Prepared into | 1,000 | granules |

Preparation Process:

1. Preparation of Raw and Auxiliary Materials

The palbociclib isethionate, the microcrystalline cellulose and the crospovidone were sifted with a 40-mesh sieve, and the lactose, the colloidal silicon dioxide and the magnesium stearate were sifted with an 80-mesh sieve for later use.

2. Premixing

The palbociclib isethionate and the microcrystalline cellulose were weighed according to the amounts in the prescription respectively, premixed, and then sifted with a 40-mesh sieve.

3. Mixing

A premix, the lactose, the crospovidone and the colloidal silicon dioxide were added to a three-dimensional motion mixer and mixed for 15 min.

4. Dry Granulation

After parameters of a dry granulation machine (with the press roll pressure set to 35-45 kg/cm$^3$) were set, a mixture obtained in step 3 was subjected to dry granulation.

5. Blending

The magnesium stearate and granules obtained after the dry granulation were added to the three-dimensional motion mixer and blended for uniform mixing for 10 min.

6. Filling of Capsules

Capsules were filled with blended granules by using a capsule filling machine, where 0 #capsules (hollow gelatin capsules produced by the manufacturer Suzhou Capsugel® LTD. were used in the example) were used, and the filling capacity was 450 mg.

Three batches of samples prepared were recorded as a sample 1-1, a sample 1-2, and a sample 1-3 respectively.

Comparative Example 1

As the palbociclib isethionate is loose and has poor fluidity, direct powder filling is difficult, and a sample is obtained by a wet granulation method in the comparative example below.

A wet granulation process is studied by using the components of the prescription in Example 1. A preparation process is as follows.

1. Preparation of Raw and Auxiliary Materials

The palbociclib isethionate, the microcrystalline cellulose and the crospovidone were sifted with a 40-mesh sieve, and the lactose, the colloidal silicon dioxide and the magnesium stearate were sifted with an 80-mesh sieve for later use.

2. Premixing

The palbociclib isethionate and the microcrystalline cellulose were weighed according to the amounts in the prescription respectively, premixed, and then sifted with a 40-mesh sieve.

3. Mixing

A premix, the lactose, the crospovidone and the colloidal silicon dioxide were added to a three-dimensional motion mixer and mixed for 15 min.

4. Wet Granulation

After parameters of a wet granulation machine were set, purified water was added to a mixture obtained in step 3 to prepare a soft material, and after a fluidized bed was adopted for drying, granules were sifted with a 24-mesh sieve and then subjected to granulation.

5. Blending

The magnesium stearate and granules obtained after the granulation were added to the three-dimensional motion mixer and blended for uniform mixing for 10 min.

6. Filling of Capsules

Capsules were filled with blended granules by using a capsule filling machine, where 0 #capsules (hollow gelatin capsules produced by the manufacturer Suzhou Capsugel® LTD. were used in the example) were used, and the filling capacity was 450 mg.

After the wet granulation is used, the fluidity of a composition is improved, but the prepared granules are still loose and have a tap density of 0.551 g/mL, an angle of repose of 39° and large volume. Matching capsule shells that can be filled with samples with larger size have not been found.

Example 2

A prescription includes the following components:

| | | |
|---|---|---|
| Palbociclib isethionate | 128.18 | g |
| Pregelatinized starch | 66.16 | g |
| Lactose | 132.32 | g |
| Crospovidone | 21.6 | g |
| Colloidal silicon dioxide | 4.56 | g |
| Magnesium stearate | 7.2 | g |
| Prepared into | 1,000 | granules |

1. Preparation of Raw and Auxiliary Materials

The palbociclib isethionate, the pregelatinized starch and the crospovidone were sifted with a 40-mesh sieve, and the lactose, the colloidal silicon dioxide and the magnesium stearate were sifted with an 80-mesh sieve for later use.

2. Premixing

The palbociclib isethionate and the pregelatinized starch were weighed according to the amounts in the prescription respectively, premixed, and then sifted with a 40-mesh sieve.

3. Mixing

A premix, the lactose, the crospovidone and the colloidal silicon dioxide were added to a three-dimensional motion mixer and mixed for 15 min.

4. Dry Granulation

After parameters of a dry granulation machine (with the press roll pressure set to 35-45 kg/cm$^3$) were set, a mixture obtained in step 3 was subjected to dry granulation.

5. Blending

The magnesium stearate and granules obtained after the dry granulation were added to the three-dimensional motion mixer and blended for uniform mixing for 10 min.

6. Filling of Capsules

Capsules were filled with blended granules by using a capsule filling machine, where 1 #capsules (hollow gelatin capsules produced by the manufacturer Suzhou Capsugel® LTD. were used in the example) were used, and the filling capacity was 360 mg.

Example 3

A prescription includes the following components:

| | | |
|---|---|---|
| Palbociclib isethionate | 96.14 | g |
| Anhydrous calcium hydrogen phosphate | 148.86 | g |
| Crospovidone | 16.2 | g |
| Talc powder | 3.42 | g |
| Sodium stearyl fumarate | 5.4 | g |
| Prepared into | 1,000 | granules |

Preparation Process:

1. Preparation of Raw and Auxiliary Materials

The palbociclib isethionate, the anhydrous calcium hydrogen phosphate and the crospovidone were sifted with a 40-mesh sieve, and the talc powder and the sodium stearyl fumarate were sifted with an 80-mesh sieve for later use.

2. Premixing

The palbociclib isethionate and the anhydrous calcium hydrogen phosphate were weighed according to the amounts in the prescription respectively, premixed, and then sifted with a 40-mesh sieve.

3. Mixing

A premix, the talc powder and the crospovidone were added to a three-dimensional motion mixer and mixed for 15 min.

4. Dry Granulation

After parameters of a dry granulation machine (with the press roll pressure set to 35-45 kg/cm$^3$) were set, a mixture obtained in step 3 was subjected to dry granulation.

5. Blending

The sodium stearyl fumarate and granules obtained after the dry granulation were added to the three-dimensional motion mixer and blended for uniform mixing for 10 min.

6. Filling of Capsules

Capsules were filled with blended granules by using a capsule filling machine, where 2 #capsules (hollow gelatin capsules produced by the manufacturer Suzhou Capsugel® LTD. were used in the example) were used, and the filling capacity was 270 mg.

Example 4

A prescription includes the following components:

| | |
|---|---|
| Palbociclib isethionate | 160.23 g |
| Lactose | 82.7 g |
| Microcrystalline cellulose | 165.4 g |
| Crospovidone | 27 g |
| Colloidal silicon dioxide | 5.7 g |
| Magnesium stearate | 9 g |
| Prepared into | 1,000 granules |

Preparation Process:

1. Preparation of Raw and Auxiliary Materials

The palbociclib isethionate, the microcrystalline cellulose and the crospovidone were sifted with a 40-mesh sieve, and the lactose, the colloidal silicon dioxide and the magnesium stearate were sifted with an 80-mesh sieve for later use.

2. Premixing

The palbociclib isethionate and the microcrystalline cellulose were weighed according to the amounts in the prescription respectively, premixed, and then sifted with a 40-mesh sieve.

3. Mixing

A premix, the lactose and the crospovidone were added to a three-dimensional motion mixer and mixed for 15 min.

4. Blending

The colloidal silicon dioxide, the magnesium stearate and a mixture obtained in step 3 were added to the three-dimensional motion mixer and blended for uniform mixing for 10 min.

5. Filling of Capsules

Capsules were filled with blended granules by using a capsule filling machine, where 0 #capsules (hollow gelatin capsules produced by the manufacturer Suzhou Capsugel® LTD. were used in the example) were used, and the filling capacity was 450 mg.

Example 5

A prescription includes the following components:

| | |
|---|---|
| Palbociclib isethionate | 160.23 g |
| Lactose | 82.7 g |
| Microcrystalline cellulose | 165.4 g |
| Crospovidone | 27 g |
| Colloidal silicon dioxide | 5.7 g |
| Magnesium stearate | 9 g |
| Prepared into | 1,000 granules |

Preparation Process:

1. Preparation of Raw and Auxiliary Materials

The palbociclib isethionate, the microcrystalline cellulose and the crospovidone were sifted with a 40-mesh sieve, and the lactose, the colloidal silicon dioxide and the magnesium stearate were sifted with an 80-mesh sieve for later use.

2. Mixing

The palbociclib isethionate, the microcrystalline cellulose, the crospovidone, the lactose and the colloidal silicon dioxide were weighed according to the amounts in the prescription respectively, added to a three-dimensional motion mixer and mixed for 20 min.

3. Blending

The magnesium stearate and a mixture obtained in step 2 were added to the three-dimensional motion mixer and blended for uniform mixing for 10 min.

4. Filling of Capsules

Capsules were filled with blended granules by using a capsule filling machine, where 0 #capsules (hollow gelatin capsules produced by the manufacturer Suzhou Capsugel® LTD. were used in the example) were used, and the filling capacity was 450 mg.

Example 6

A prescription includes the following components:

| | |
|---|---|
| Palbociclib isethionate | 160.2 g |
| Pregelatinized starch | 92.7 g |
| Microcrystalline cellulose | 155.1 g |
| Sodium carboxymethyl starch | 27 g |
| Sodium stearyl fumarate | 9 g |
| Prepared into | 1,000 granules |

Preparation Process:

1. Preparation of raw and auxiliary materials

The palbociclib isethionate, the microcrystalline cellulose and the sodium carboxymethyl starch were sifted with a 40-mesh sieve, and the pregelatinized starch and the sodium stearyl fumarate were sifted with an 80-mesh sieve for later use.

2. Premixing

The palbociclib isethionate and the microcrystalline cellulose were weighed according to the amounts in the prescription respectively, premixed, and then sifted with a 40-mesh sieve.

3. Mixing

A premix, the pregelatinized starch and the sodium carboxymethyl starch were added to a three-dimensional motion mixer and mixed for 15 min.

4. Dry Granulation

After parameters of a dry granulation machine (with the press roll pressure set to 35-45 kg/cm$^3$) were set, a mixture obtained in step 3 was subjected to dry granulation.

5. Blending

The sodium stearyl fumarate and granules obtained after the dry granulation were added to the three-dimensional motion mixer and blended for uniform mixing for 10 min.

6. Filling of Capsules

Capsules were filled with blended granules by using a capsule filling machine, where 0 #capsules (hollow gelatin capsules produced by the manufacturer Suzhou Capsugel® LTD. were used in the example) were used, and the filling capacity was 444 mg.

Example 7

A prescription includes the following components:

| | | |
|---|---|---|
| Palbociclib isethionate | 128.18 | g |
| Calcium hydrogen phosphate | 96.16 | g |
| Microcrystalline cellulose | 102.32 | g |
| Calcium carboxymethyl cellulose | 21.6 | g |
| Colloidal silicon dioxide | 4.56 | g |
| Magnesium stearate | 7.2 | g |
| Prepared into | 1,000 | granules |

Preparation Process:

1. Preparation of Raw and Auxiliary Materials

The palbociclib isethionate, the microcrystalline cellulose and the calcium carboxymethyl cellulose were sifted with a 40-mesh sieve, and the calcium hydrogen phosphate, the colloidal silicon dioxide and the magnesium stearate were sifted with an 80-mesh sieve for later use.

2. Premixing

The palbociclib isethionate and the microcrystalline cellulose were weighed according to the amounts in the prescription respectively, premixed, and then sifted with a 40-mesh sieve.

3. Mixing

A premix, the calcium hydrogen phosphate and the calcium carboxymethyl cellulose were added to a three-dimensional motion mixer and mixed for 15 min.

4. Dry Granulation

After parameters of a dry granulation machine were set, a mixture obtained in step 3 was subjected to dry granulation. The press roll pressure was set to 25-35 $kg/cm^3$, 35-45 $kg/cm^3$, 45-55 $kg/cm^3$, 55-65 $kg/cm^3$, and 65-70 $kg/cm^3$ separately to obtain five batches of dry granulated samples.

5. Blending

The colloidal silicon dioxide, the magnesium stearate and five batches of granules obtained after the dry granulation were separately added to the three-dimensional motion mixer and blended for uniform mixing for 10 min.

6. Filling of Capsules

Capsules were filled with blended granules by using a capsule filling machine, where 1 #capsules (hollow gelatin capsules produced by the manufacturer Suzhou Capsugel® LTD. were used in the example) were used, and the filling capacity was 360 mg.

Example 8

A prescription includes the following components:

| | | |
|---|---|---|
| Palbociclib isethionate | 96.14 | g |
| Lactose | 69.62 | g |
| Pregelatinized starch | 79.24 | g |
| Crospovidone | 10.2 | g |
| Low-substituted hydroxypropyl cellulose | 6.0 | g |
| Polyethylene glycol 3350 | 3.42 | g |
| Magnesium stearate | 5.4 | g |
| Prepared into | 1,000 | granules |

Preparation Process:

1. Preparation of Raw and Auxiliary Materials

The palbociclib isethionate, the pregelatinized starch and the crospovidone were sifted with a 40-mesh sieve, and the lactose and the magnesium stearate were sifted with an 80-mesh sieve for later use.

2. Premixing

The palbociclib isethionate and the pregelatinized starch were weighed according to the amounts in the prescription respectively, premixed, and then sifted with a 40-mesh sieve.

3. Mixing

A premix, the lactose, the crospovidone, the low-substituted hydroxypropyl cellulose and the polyethylene glycol 3350 were added to a three-dimensional motion mixer and mixed for 15 min.

4. Dry Granulation

After parameters of a dry granulation machine (with the press roll pressure set to 35-45 $kg/cm^3$) were set, a mixture obtained in step 3 was subjected to dry granulation.

5. Blending

The magnesium stearate and granules obtained after the dry granulation were added to the three-dimensional motion mixer and blended for uniform mixing for 10 min.

6. Filling of Capsules

Capsules were filled with blended granules by using a capsule filling machine, where 2 #capsules (hollow gelatin capsules produced by the manufacturer Suzhou Capsugel® LTD. were used in the example) were used, and the filling capacity was 270 mg.

Example 9

A prescription includes the following components:

| | | |
|---|---|---|
| Palbociclib isethionate | 160.23 | g |
| Lactose | 82.7 | g |
| Microcrystalline cellulose | 165.4 | g |
| Crospovidone | 27 | g |
| Colloidal silicon dioxide | 5.7 | g |
| Magnesium stearate | 9 | g |
| Prepared into | 1,000 | granules |

Preparation Process:

1. Preparation of Raw and Auxiliary Materials

The palbociclib isethionate, the microcrystalline cellulose and the crospovidone were sifted with a 40-mesh sieve, and the lactose, the colloidal silicon dioxide and the magnesium stearate were sifted with an 80-mesh sieve for later use.

2. Mixing

The palbociclib isethionate, the microcrystalline cellulose, the lactose, the crospovidone and the colloidal silicon dioxide were weighed according to the amounts in the prescription respectively, added to a three-dimensional motion mixer and mixed for 15 min.

3. Dry Granulation

After parameters of a dry granulation machine (with the press roll pressure set to 35-45 $kg/cm^3$) were set, a mixture obtained in step 2 was subjected to dry granulation.

4. Blending

The magnesium stearate and a mixture obtained after the dry granulation were added to the three-dimensional motion mixer and blended for uniform mixing for 10 min.

5. Filling of Capsules

Capsules were filled with blended granules by using a capsule filling machine, where 0 #capsules (hollow gelatin capsules produced by the manufacturer Suzhou Capsugel® LTD. were used in the example) were used, and the filling capacity was 450 mg.

It should be pointed out that the glidant in the examples may be not added, or be added before or after the dry granulation. The lubricant may be added before or after the dry granulation. The use of the glidant and/or the lubricant is combined with the component ratios, premixing and dry granulation to ensure that the granules before filling of capsules have a tap density of 0.55-0.72 and an angle of repose of less than or equal to 44°.

The following studies are carried out on the samples prepared in the examples 1-9 above.

I. Comparative Study on Different Press Roll Pressures

With reference to Example 7, 5 batches of samples 7-1, 7-2, 7-3, 7-4, and 7-5 were prepared by a capsule filling process after granules were prepared by dry granulation at different press roll pressures (a GL5-50 dry granulation machine with a 2.0 mm primary granulation sieve and a 1.0 mm secondary granulation sieve was used), and properties of the granules (including angle of repose, bulk density, and tap density), content uniformity of finished products, and other indexes were investigated separately. Results show that the five samples prepared by the dry granulation at different press roll pressures can be better filled. According to requirements of pharmacopoeia, the release rate of the samples is equal to or greater than 80% (Q) of the labelled amount in a medium with a pH of 1.2 within 30 minutes. Thus, the release rate of the various batches of samples (7-1, 7-2, 7-3, 7-4, and 7-5) was investigated in a medium with a pH of 1.2. Results show that the release of all the samples is qualified. Results are as shown in Table 1 and FIG. 1 below.

FIG. 1 shows that capsules are filled with granules prepared from the prescription powder mix of the present invention by dry granulation at a press roll pressure of 25-65 kg/cm$^3$, and the prepared samples have basically consistent in vitro release behaviors in a medium with a pH of 1.2.

Therefore, when the press roll pressure is controlled in the range of 25-65 kg/cm$^3$ in the dry granulation process with the same dry granulation machine as that in the example, samples which have good fluidity and are easily filled into capsules can be obtained.

II. Determination of the Content Uniformity of Products Prepared by Different Mixing Processes of Raw Materials and Auxiliary Materials The samples prepared by dry granulation in Example 1 and Example 9 and the samples prepared by direct powder filling in Example 4 and Example 5 were taken, and 10 capsules of each sample were taken to determine the content uniformity. As shown in Table 2, results indicate that: the samples prepared by premixing the raw material of palbociclib isethionate with the microcrystalline cellulose and then conducting sifting in Example 1 and Example 4 have a smaller RSD value of the measured content uniformity, and mixing of the powder mix is more uniform. However, both the samples prepared by dry granulation in Example 1 and Example 9 have a smaller RSD value of the content uniformity than the samples prepared by a direct powder filling process. The samples prepared by premixing the raw material of palbociclib isethionate with the microcrystalline cellulose (JRS12) and then conducting sifting, followed by dry granulation in Example 1 have good content uniformity. Therefore, a preparation process preferably includes premixing the raw material of palbociclib isethionate with the microcrystalline cellulose and then conducting sifting, followed by dry granulation. Specific test results are as shown in Table 2.

TABLE 1

| Sample | Sample 7-1 | Sample 7-2 | Sample 7-3 | Sample 7-4 | Sample 7-5 |
|---|---|---|---|---|---|
| Press roll pressure (kg/cm$^3$) | 25-35 | 35-45 | 45-55 | 55-65 | 65-70 |
| Powder mix angle of repose (°) | 38 | 36 | 37 | 37 | 38 |
| Bulk density (g/cm$^3$) | 0.530 | 0.578 | 0.621 | 0.640 | 0.650 |
| Tap density (g/cm$^3$) | 0.620 | 0.650 | 0.690 | 0.720 | 0.741 |
| Compression index | 14.5 | 11.1 | 10.0 | | |
| Filling property | Capsules have good filling conditions | Capsules have good filling conditions | Capsules have good filling conditions | Capsules have good filling conditions | Capsules have good filling conditions |
| Loading difference (limit requirement ± 7.5%) | −2.3% to 4.7% | −3.0% to 2.1% | −1.3% to 2.9% | −1.0% to 1.2% | −1.2% to 1.1% |
| Content uniformity (limit requirement A + 2.2S ≤ 15) | 6.1 | 5.7 | 2.7 | 2.4 | 2.5 |
| Disintegration time (min) | 2 min 50 s | 3 min 30 s | 5 min 46 s | 10 min | 16 min |

The above study data indicate that the prescription powder mix of the present invention has good compressibility in dry granulation at a press roll pressure of 25-65 kg/cm$^3$, the granular powder mix prepared has good fluidity and can be easily filled into capsules, a filling process is stable, filled capsules have small differences, the content uniformity of the samples meets requirements of a content uniformity test method of General Rule 0941 of Pharmacopoeia (2015 edition), and the disintegration time is shorter than 15 min. With further increase of the pressure, the disintegration time is prolonged, resulting in decrease of the dissolution rate.

TABLE 2

| | Example 1 Premixing of a raw material with microcrystalline cellulose and sifting | | Example 9 Without processes of premixing and sifting | |
|---|---|---|---|---|
| | Average content (%) | RSD % | Average content (%) | RSD % |
| Dry granulation and filling | 100.3 | 1.5 | 100.9 | 3.9 |
| | **Example 4 Premixing of a raw material with microcrystalline cellulose and sifting** | | **Example 5 Without processes of premixing and sifting** | |
| | **Average content (%)** | **RSD %** | **Average content (%)** | **RSD %** |
| Direct powder filling | 102.3 | 4.7 | 97.2 | 7.3 |

III. Comparison of the Quality of Products Prepared By Different Preparation Processes The palbociclib isethionate has poor fluidity and is a loose powder. When capsules are filled by direct powder filling, it is found that the capsules are difficult to fill. Especially when capsules are filled in commercial batches in a large scale, the problem of difficulty in automatic filling at high speed will be caused due to poor fluidity of the powder. Moreover, the filled capsules have great differences in loading capacity, so that the content uniformity and the product quality are unqualified. After studies, it has been found that the problem can be better solved by filling capsules after dry granulation. Study results are as shown in Table 3.

The above study data indicate that: a powder mix prepared by a direct powder filling process has poor fluidity and great differences in loading capacity in a filling process, and cannot be better filled. Different samples have great differences in content, and some samples are unqualified. After dry granulation, a prepared powder mix has good granular fluidity, capsules have good conditions in a filling process, various investigated indexes meet limit requirements, and samples are qualified. However, when a powder mix is not subjected to premixing treatment before dry granulation and all materials are directly mixed, a main medicine has slightly worse fluidity than the samples with premixing treatment, but still has good fluidity, so that the filling of capsules can be ensured.

TABLE 3

| Preparation process | Dry granulation and filling (premixing) | Direct powder filling (premixing) | Direct powder filling (without premixing) | Dry granulation and filling (without premixing) | Dry granulation and filling (premixing) | Dry granulation and filling (premixing) | Dry granulation and filling (premixing) | Dry granulation and filling (premixing) |
|---|---|---|---|---|---|---|---|---|
| Sample | Example 1 | Example 4 | Example 5 | Example 9 | Example 2 | Example 3 | Example 6 | Example 8 |
| Powder mix angle of repose (°) | 37 | 48 | 47 | 44 | 36 | 37 | 38 | 37 |
| Bulk density (g/cm$^3$) | 0.552 | 0.476 | 0.481 | 0.509 | 0.554 | 0.551 | 0.550 | 0.559 |
| Tap density (g/cm$^3$) | 0.670 | 0.509 | 0.511 | 0.567 | 0.671 | 0.663 | 0.676 | 0.669 |
| Filling property | Capsules have good filling conditions | Capsules cannot be better filled | Capsules cannot be better filled | Capsules can be better filled | Capsules have good filling conditions | Capsules have good filling conditions | Capsules have good filling conditions | Capsules have good filling conditions |
| Loading difference (limit requirement ± 7.5%) | −3.2% to 2.9% | −11.0% to 8.3% | −14.0% to 13.4% | −5.5% to 5.9% | −3.0% to 2.8% | −2.1% to 2.0% | −2.4% to 3.6% | −2.2% to 1.3% |
| Content uniformity (limit requirement A + 2.2S ≤ 15) | 5.0 | 15.2 | 16.9 | 14.3 | 3.4 | 4.2 | 3.7 | 4.9 |

IV. Study On Inter-batch Uniformity and Intra-batch Uniformity 3 batches of samples (samples 1-1, 1-2, and 1-3) were prepared by a dry granulation and capsule filling process with reference to Example 1, the loading difference, content uniformity, and other indexes were investigated separately to illustrate the intra-batch uniformity, and meanwhile, the release rate of each batch of samples was investigated in a medium with a pH of 1.2 to illustrate the inter-batch uniformity. The samples were weighed on the standard that the release rate is equal to or greater than 80% (Q) in a medium with a pH of 1.2 within 30 minutes. Results show that both the intra-batch uniformity and the inter-batch uniformity are good. Results are as shown in Table 4 and FIG. 2.

TABLE 4

| Sample | Sample 1-1 | Sample 1-2 | Sample 1-3 |
|---|---|---|---|
| Powder mix angle of repose (°) | 36 | 37 | 36 |
| Bulk density (g/cm$^3$) | 0.557 | 0.558 | 0.551 |
| Tap density (g/cm$^3$) | 0.651 | 0.660 | 0.655 |
| Filling property | Capsules have good filling conditions | Capsules have good filling conditions | Capsules have good filling conditions |
| Loading difference (limit requirement ± 7.5%) | −2.0% to 2.7% | −3.2% to 2.9% | −2.3% to 3.9% |
| Content uniformity (limit requirement A + 2.2S ≤ 15) | 4.3 | 5.0 | 3.9 |
| Disintegration time (min) | 3 min 50 s | 3 min | 3 min 10 s |

The above study data show that the 3 batches of samples prepared continuously by the same prescription process have basically same investigation indexes, indicating that the prescription process of the present invention has good feasibility and high reproducibility.

Figure 2:
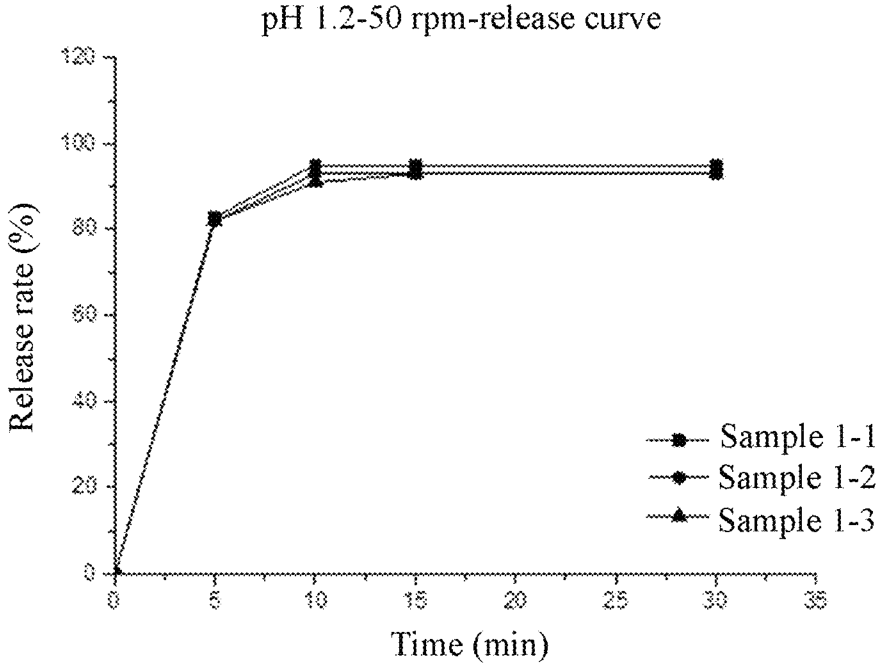
FIG. 2 shows release curves of 3 batches of samples in Example 1 in a medium with a pH of 1.2.
Figure 3:
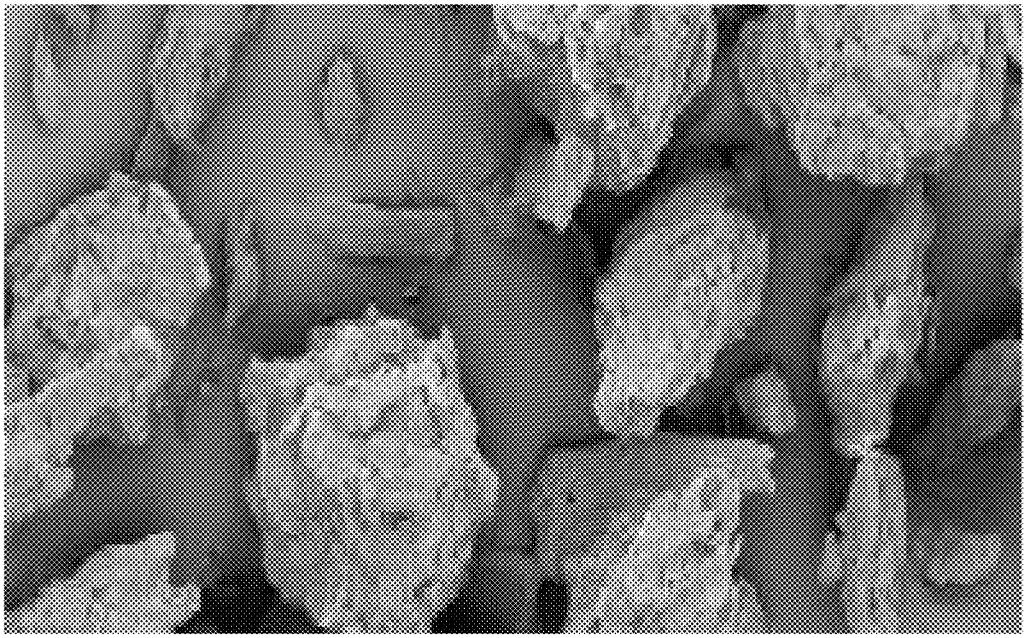
FIG. 3 is a scanning electron microscopy (SEM) image of porous granular microcrystalline cellulose.

FIG. 2 shows that the 3 batches of samples prepared by the same prescription process have basically consistent in vitro release behaviors in a medium with a pH of 1.2.

Therefore, samples having stable quality can be continuously produced according to the present invention.

V. Quality Investigation

Quality investigation was carried out on the 3 batches of samples (samples 1-1, 1-2, and 1-3) prepared by a dry granulation and capsule filling process with reference to Example 1 and palbociclib capsules in a free alkali form produced by Pfizer (commercially available product Ibrance with a specification of 125 mg). Results show that the total impurity content is basically the same.

TABLE 5

| Sample | Maximum unknown single impurity | Total impurities (%) |
|---|---|---|
| Pfizer Original Research (X52432) | 0.02 | 0.20 |
| Sample 1-1 | 0.02 | 0.16 |
| Sample 1-2 | 0.02 | 0.14 |
| Sample 1-3 | 0.02 | 0.15 |

The above content is a schematic description of the present invention and embodiments thereof, and the description is not restrictive. The content as shown in the examples is only one of the embodiments of the present invention, and the embodiments are actually not limited thereto. Therefore, when those of ordinary skill in the art are inspired by the present invention, structural modes and examples made similar to the technical solutions without creative design on the premise of not departing from the creative purpose of the present invention shall fall within the protection scope of the present invention.

What is claimed is:

1. A process for improving the fluidity of palbociclib isethionate, comprising step of conducting dry granulation on palbociclib isethionate and pharmaceutically acceptable auxiliary materials to obtain granules with a tap density of 0.62-0.69 g/mL and an angle of repose of less than or equal to 44°;

the auxiliary materials comprise a diluent, a disintegrant, a glidant, and a lubricant;

wherein the palbociclib isethionate is premixed first with the diluent, and a mass ratio of the palbociclib isethionate to the diluent during premixing is 1:(0.8-2.0);

and a premix obtained after premixing is mixed with other auxiliary materials, and then dry granulation is conducted to obtain granules before filling of capsules, wherein the granules before filling of capsules have a tap density of 0.62-0.69 g/mL and an angle of repose of less than or equal to 44°;

or a premix obtained after premixing is mixed with other auxiliary materials except for the glidant and the lubricant, dry granulation is conducted to obtain dry granulated granules, and then the glidant and the lubricant are added for mixing to obtain granules before filling of capsules, wherein the granules before filling of capsules have a tap density of 0.62-0.69 g/mL and an angle of repose of less than or equal to 44°;

or a premix obtained after premixing is mixed with other auxiliary materials except for the lubricant, dry granulation is conducted to obtain dry granulated granules, and then the lubricant is added for mixing to obtain granules before filling of capsules, wherein the granules before filling of capsules have a tap density of 0.62-0.69 g/mL and an angle of repose of less than or equal to 44°;

wherein the diluent is selected from one or more of lactose, microcrystalline cellulose, pregelatinized starch, mannitol or calcium hydrogen phosphate, and at least one diluent is highly porous granular microcrystalline cellulose;

the disintegrant is selected from one or more of crospovidone, sodium carboxymethyl starch, crosslinked sodium carboxymethyl cellulose, calcium carboxymethyl cellulose or low-substituted hydroxypropyl cellulose;

the lubricant is selected from one or more of magnesium stearate, sodium stearyl fumarate, calcium stearate and stearic acid; the glidant is selected from one or more of silicon dioxide, talc powder or polyethylene glycol; and a composition comprises 40-70 parts by mass of the diluent, 1-15 parts by mass of the disintegrant, 0.1-10 parts by mass of the lubricant, 0.5-10 parts by mass of the glidant, and 25-50 parts by mass of the palbociclib isethionate.

2. The process for improving the fluidity of palbociclib isethionate according to claim 1, wherein before the dry granulation, the premix is mixed with other auxiliary materials in a three-dimensional motion mixer for 10-30 min.

3. The process for improving the fluidity of palbociclib isethionate according to claim 1, wherein the dry granulation is conducted by using a GL5-50 dry granulation machine with a 2.0 mm primary granulation sieve and a 1.0 mm secondary granulation sieve at a press roll pressure of 25-65 $kg/cm^3$.

4. The process for improving the fluidity of palbociclib isethionate according to claim 1, wherein before the palbociclib isethionate is premixed first with the diluent, the process further comprises: a step of sifting the palbociclib isethionate, the disintegrant, the diluent, the lubricant and the glidant for later use.

5. The process for improving the fluidity of palbociclib isethionate according to claim 4, wherein in the premixing step, when a composition contains one diluent, the palbociclib isethionate is premixed first with the diluent completely, and then sifting is conducted to obtain a premix;

and when a composition contains two or more diluents, the palbociclib isethionate is premixed first with all the diluents, or the palbociclib isethionate is premixed first with one of the diluents, and then sifting is conducted to obtain a premix.

6. The process for improving the fluidity of palbociclib isethionate according to claim 4, wherein in the premixing step, when a composition contains two or more diluents, the palbociclib isethionate is premixed first with one diluent with the highest content among the diluents, and then sifting is conducted to obtain a premix.

7. The process for improving the fluidity of palbociclib isethionate according to claim 1, wherein 50-60 parts by mass of the diluent, 3-10 parts by mass of the disintegrant, 0.5-4 parts by mass of the lubricant, 0.5-5 parts by mass of the glidant, and 30-45 parts by mass of the palbociclib isethionate are used.

8. The process according to claim 1, wherein the diluent comprises lactose and highly porous granular microcrystalline cellulose, the disintegrant is crospovidone, the glidant is colloidal silicon dioxide, and the lubricant is magnesium stearate.

9. The process according to claim 8, further comprising filling capsules with the granules, wherein a loading difference of the filled capsules is within +7.5% and a disintegration time of the filled capsules is less than 15 minutes.

* * * * *